United States Patent
Lawyer et al.

(10) Patent No.: US 10,933,109 B2
(45) Date of Patent: Mar. 2, 2021

(54) COMPOSITIONS AND METHODS FOR SLEEP DISORDERS AND RESTLESS LEG SYNDROMES

(71) Applicants: Matthew Carl Lawyer, Park City, UT (US); Carl Henry Lawyer, Park City, UT (US); Edward George Robertshaw, Park City, UT (US)

(72) Inventors: Matthew Carl Lawyer, Park City, UT (US); Carl Henry Lawyer, Park City, UT (US); Edward George Robertshaw, Park City, UT (US)

(*) Notice: Subject to any disclaimer, the term of this patent is extended or adjusted under 35 U.S.C. 154(b) by 0 days.

(21) Appl. No.: 15/691,745

(22) Filed: Aug. 31, 2017

(65) Prior Publication Data
US 2020/0093880 A1   Mar. 26, 2020

Related U.S. Application Data

(60) Provisional application No. 62/381,949, filed on Aug. 31, 2016.

(51) Int. Cl.
*A61K 36/00* (2006.01)
*A61K 36/60* (2006.01)
*A61P 25/20* (2006.01)

(52) U.S. Cl.
CPC ............ *A61K 36/60* (2013.01); *A61P 25/20* (2018.01)

(58) Field of Classification Search
None
See application file for complete search history.

(56) References Cited

U.S. PATENT DOCUMENTS

2012/0128808 A1* 5/2012 Gokaraju ............... A61K 36/60
424/777

* cited by examiner

*Primary Examiner* — Qiuwen Mi

(57) ABSTRACT

Methods of treating or preventing at least one sign or symptom of restless leg syndrome or related disorders are disclosed. The methods comprise identifying a host, afflicted with restless leg syndrome or related disorders; and administering to the host a pharmaceutically effective amount of a fruit of *Ficus carica* plant or an extract thereof. Also provided are methods and compositions for treating or preventing sleep disorders, and methods and compositions for improving sleep adequacy and quantity.

7 Claims, 5 Drawing Sheets

COMPOSITIONS AND METHODS FOR SLEEP DISORDERS AND RESTLESS LEG SYNDROMES

PRIORITY

This application claims priority of U.S. Provisional Patent Application Ser. No. 62/381,949 filed Aug. 31, 2016 titled "COMPOSITIONS AND METHODS FOR SLEEP DISORDERS AND RESTLESS LEG SYNDROME", the teachings of which are incorporated herein by reference.

TECHNICAL FIELD OF INVENTION

The present invention relates to compositions and methods for treating or preventing restless leg syndrome, sleep disorders, and related diseases and disorders, and for the occurrence of unwanted limb movement. In various embodiments, the present invention provides methods and compositions for treating sleep disorders, and improving sleep quantity and adequacy by administering a fig or a fig extract to a subject. In various embodiments, the present invention relates to the use of a fig, and in various embodiments to the use of a fig extract, for treating restless leg syndrome, and related diseases and disorders.

BACKGROUND

Sleeping disorders are a major problem for our society. Sleeping disorders including not getting enough sleep, not feeling well-rested, not sleeping with a sufficient quality of sleep, and waking during the course of sleep night. Sleep disorders can lead to difficulties functioning during the daytime and have unpleasant secondary effects on the social, work, and family quality of life for the subject suffering from the sleep disorder. In addition to affecting the quality and quantity of sleep itself, many medical and mental health conditions can be worsened by sleep and sleep-related disorders. A common type of sleep disorder is insomnia. Insomnia is an inability to get the amount of sleep needed to function efficiently or effectively during the daytime. Difficulty sleeping is a common deleterious affliction. Insomnia may be caused by difficulty falling asleep, difficulty staying asleep or waking up too early in the morning. Short-term time periods of insomnia are an even more common affliction and may relate to temporary stressors, travel (e.g., time zone differences) or other events. A sufficient quantity of high quality sleep is necessary for recovery—or prevention of many illnesses, including mental illness. Insomnia and other sleep disorders may be associated with depression, anxiety or psychological stress. Restless legs syndrome (RLS), also called Willis-Ekbom Disease, causes unpleasant or uncomfortable sensations in the legs and an irresistible urge to move them. RLS is typically associated with sleep disorders. Symptoms commonly occur in the late afternoon or evening hours, and are often most severe at night when a person is resting, such as sitting or lying in bed. They also may occur when someone is inactive and sitting for extended periods (for example, when taking a trip by plane or watching a movie). Symptoms of RLS can increase in severity during the night. The consequence is that the subject may have difficulty falling asleep or return to sleep after waking up due to the discomforting symptoms of RLS. Moving of the legs or walking may typically relieve discomfort but the negative sensations or pain often recur once the movement stops. RLS may include symptoms that are triggered by resting and attempting to sleep and subsequent temporary symptom relief by moving legs. RLS may be viewed as a sensory/neurological disorder with symptoms that are produced from within the brain itself. RLS can cause daytime sleepiness or exhaustion, which can negatively influence affect, concentration, travel, work and scholastic performance and can contribute to depression and anxiety. Professional and personal relationship may suffer due to RLS. RLS sufferers may also have impaired memory and decreased ability to accomplish daily tasks. About one-twentieth to one-tenth of the United States population has clinical symptoms of RLS. RLS is generally a lifelong condition for which there is no cure, though current therapies may help control the disorder, minimize symptomology, and increase periods of restful sleep, these all have serious drawbacks. Most of the pharmacologic interventions have potentially dangerous or severe side effects and/or loss of efficacy over time. Symptoms may gradually worsen with age. Unlike prior proposed remedies, the instant invention provides a safe and effective remedy for sleep disorders and RLS.

SUMMARY OF THE INVENTION

In exemplary embodiments, the present invention provides compositions and methods for the treatment or prevention of diseases, such as restless leg syndrome, by administering a fig or a fig extract in a subject with such a disease. In various embodiments, the present invention also provides compositions and methods for improvement of sleep adequacy and sleep quantity, and treatment of sleep disorders by administering a therapeutically effective amount of a fig or a fig extract to a subject.

This invention encompasses methods of treating and preventing diseases, disorders and conditions that are ameliorated by the administration of a patient in need of such treatment or prevention a therapeutically or prophylactically effective amount of a fig or fig extract. In specific methods of the invention, the fig or the fig extract is optionally administered in combination with an additional pharmacologically active compound.

The present invention further encompasses pharmaceutical compositions and dosage forms which can be used, for example, in the methods disclosed herein. Exemplary pharmaceutical compositions of the present invention comprise a therapeutically or prophylactically effective amount of a fig or a fig extract and optionally an additional pharmacologically active compound.

These and other aspects of the present invention will become evident upon reference to the following detailed description. In addition, various references are set forth herein which describe in more detail certain procedures or compositions, and are therefore incorporated by reference in their entirety.

DETAILED DESCRIPTION OF INVENTION

Figure 1:
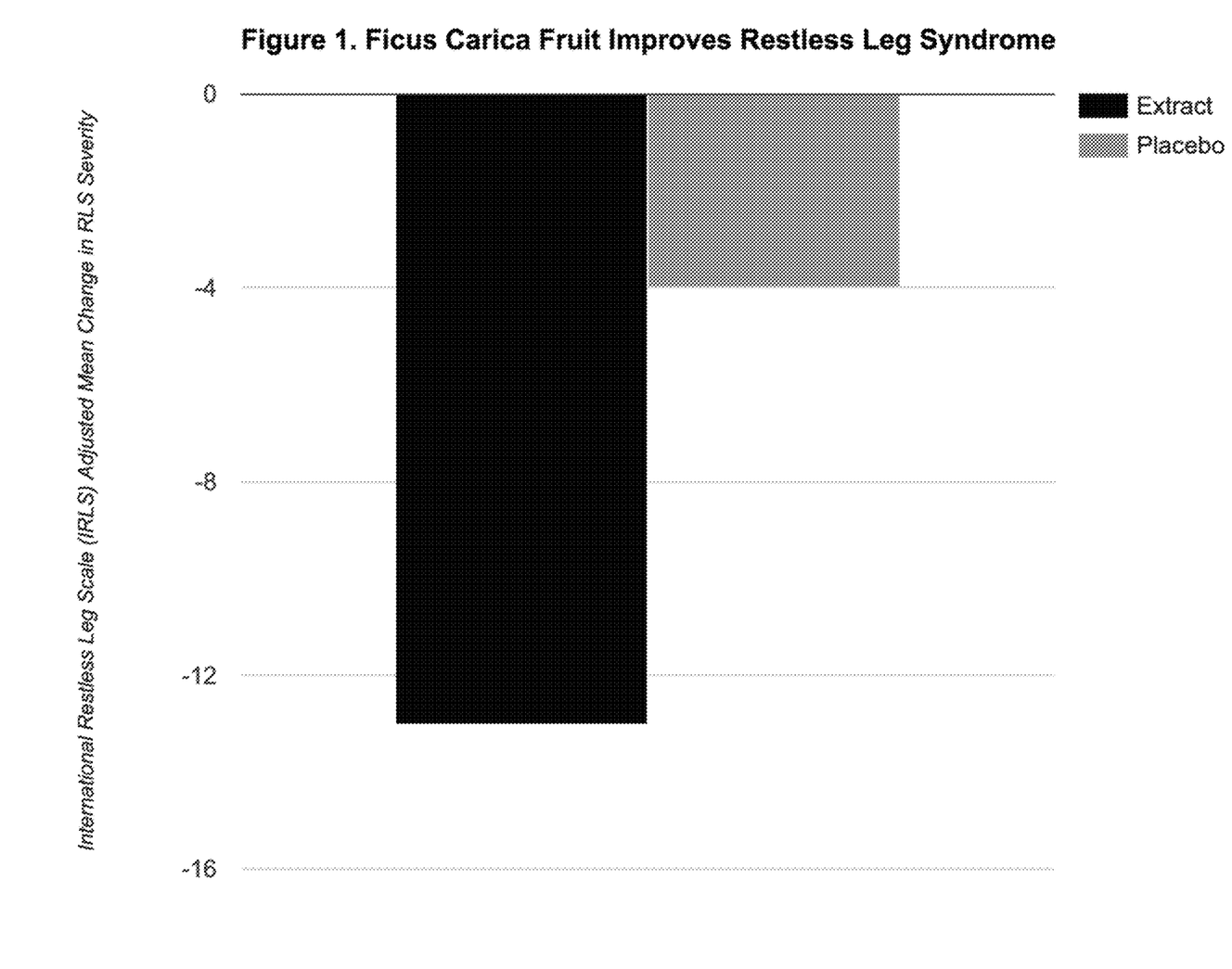
FIG. 1 (i.e., FIG. 1) depicts a graphical display of restless leg syndrome parameters showing improvement in the restless leg syndrome parameters upon administration of a fig extract.
Figure 2:
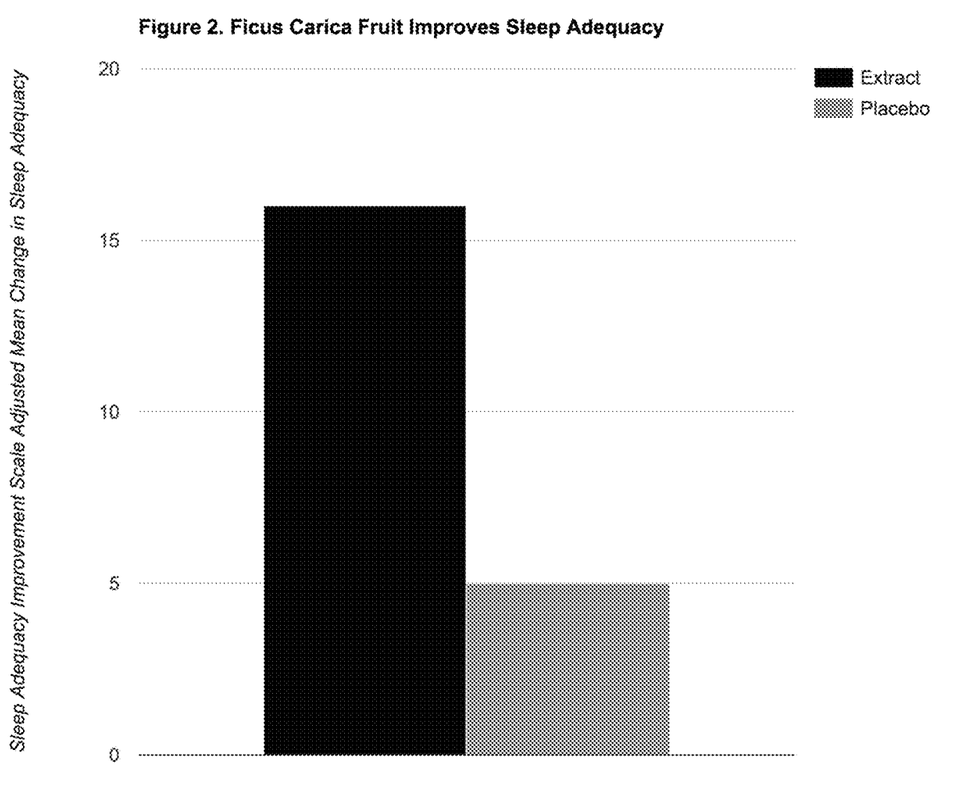
FIG. 2 (i.e., FIG. 2) depicts a graphical display of sleep adequacy parameters showing improvement in the sleep adequacy parameters upon administration of a fig extract.
Figure 3:
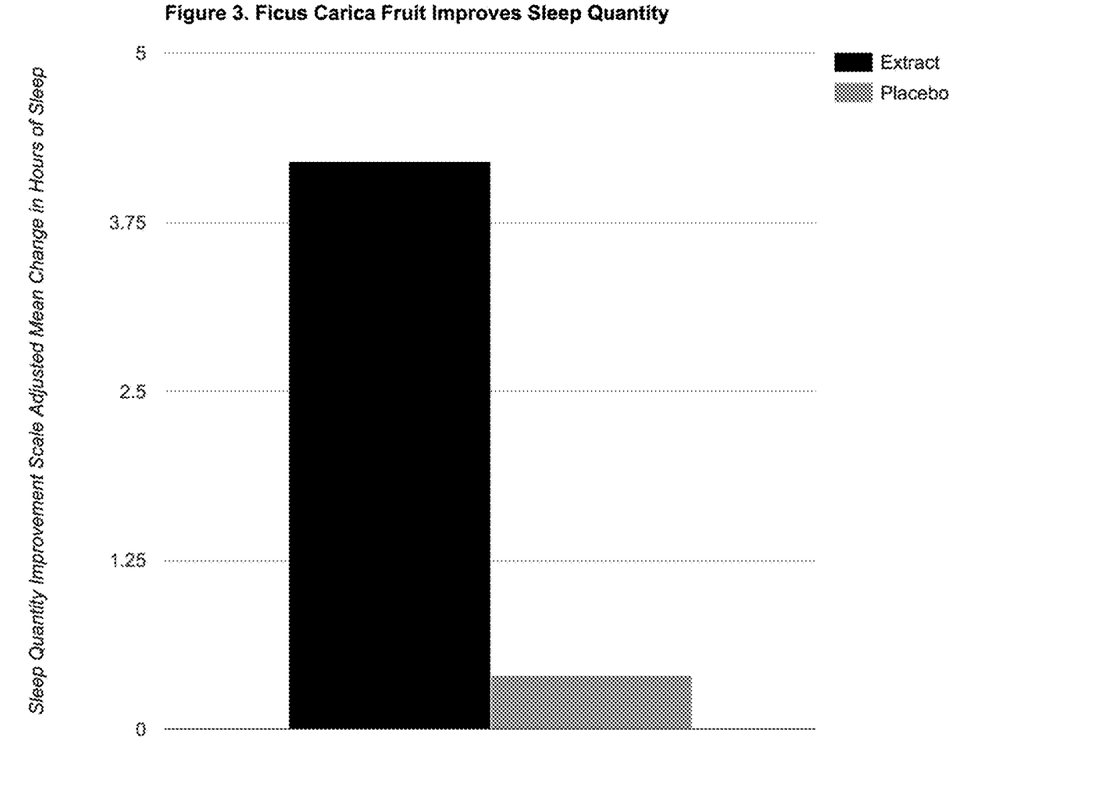
FIG. 3 (i.e., FIG. 3) depicts a graphical display of sleep quantity parameters showing improvement in the sleep quantity parameters upon administration of a fig extract.
Figure 4:
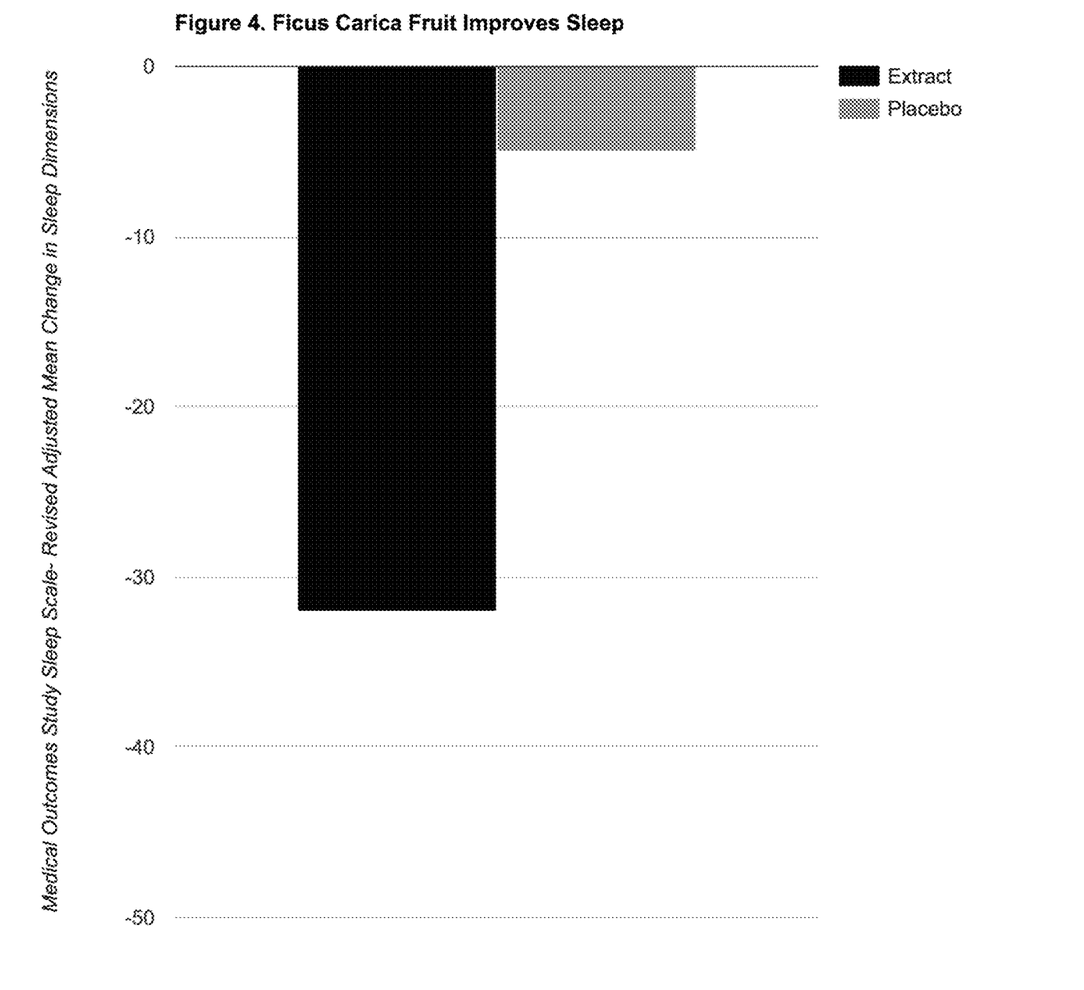
FIG. 4 (i.e., FIG. 4) depicts a graphical display of sleep parameters showing improvement in the sleep parameters upon administration of a fig extract.
Figure 5:
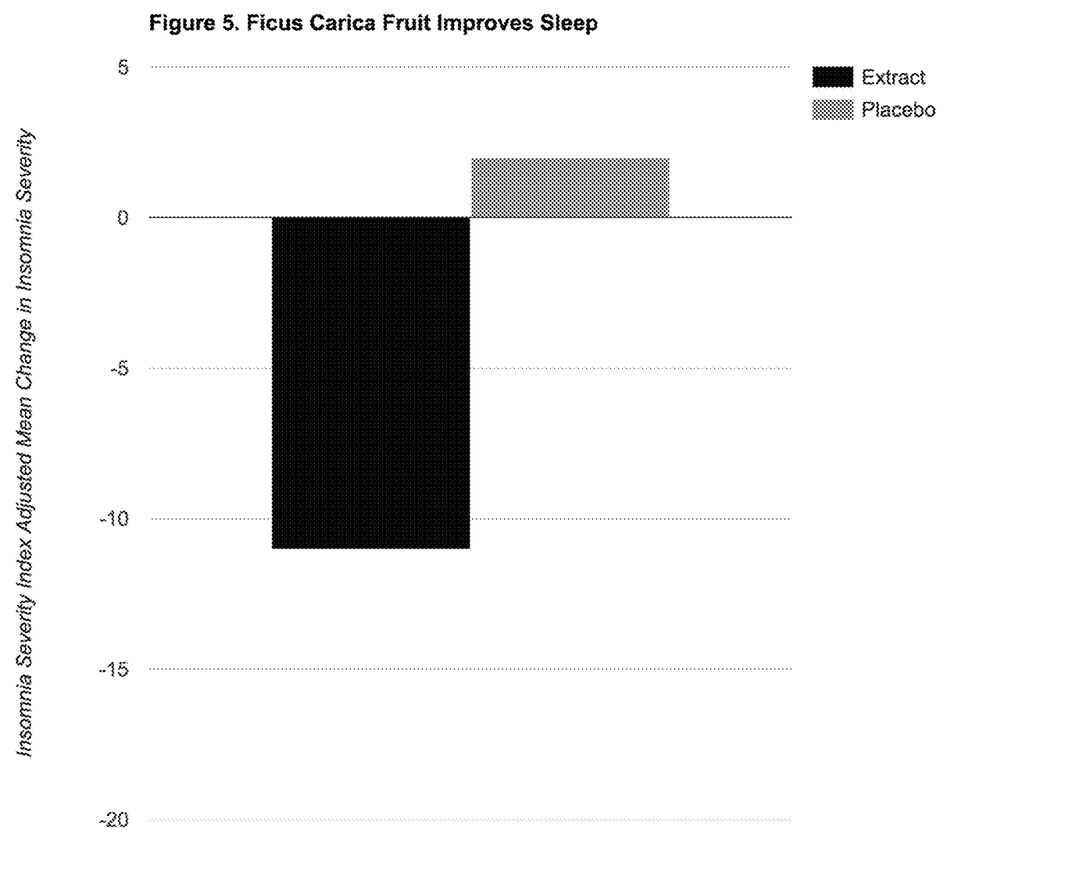
FIG. 5 (i.e., FIG. 5) depicts a graphical display of sleep parameters showing improvement in the sleep parameters upon administration of a fig extract.

As used herein, unless otherwise specified, the terms "a" or "an" mean "one or more."

As used herein, unless otherwise specified, the terms "or" and "and/or" mean "either or both." An "or" operator returns a true value when one or both operands are true. The "and" logical operator, returns a true value only when both operands are true.

As used herein, the term "comprising" means "consisting at least in part of." When interpreting statements containing the term "comprising", other features besides the features prefaced by the term "comprising" in each statement can also be present. Related terms (such as, e.g., "comprise", "comprises", "comprised", "including", "include", "includes") are to be interpreted in similar non-limiting manner.

As used herein, the term "consisting of" means including, and limited to, whatever follows the phrase "consisting of". Thus, the phrase "consisting of" indicates that the listed elements are required (i.e., mandatory), and that no other elements may be present.

As used herein, the term "consisting essentially of" means including any elements listed after the phrase, and limited to other elements that do not interfere with or contribute to the activity or action specified in the disclosure for the listed elements. Thus, the phrase "consisting essentially of" indicates that the listed elements are required (i.e., mandatory), but that no other elements are optional and may or may not be present depending upon whether or not the other elements affect the activity or action of the listed elements.

As used herein, the terms "one embodiment," "an embodiment," "an exemplary embodiment", "a particular embodiment", "a related embodiment," "an additional embodiment," "a further embodiment," "a still further embodiment", or "a yet further embodiment" or combinations thereof mean that a particular feature, structure or characteristic described in connection with the embodiment is included in at least one embodiment of the present invention. Thus, the appearances of the foregoing phrases in various places throughout herein are not necessarily all referring to the same embodiment. Furthermore, the particular features, structures, or characteristics may be combined in any suitable manner in one or more embodiments.

The practice of the present invention will employ, unless otherwise indicated, conventional methods of medical science, biochemistry, phytochemistry, nutraceutical formulation, pharmaceutical formulation, fruit extraction, pharmacology, within the ordinary skill of the art.

The terms "effective amount" or "pharmaceutically effective amount" refer to a nontoxic but sufficient amount of an agent to provide a desired biological result and, which has a clinically acceptable safety margin with respect to doses or amounts which can produce unacceptable adverse effects (e.g., toxicity) to a subject. The desired biological result can be reduction and/or alleviation of the signs, symptoms, or causes of a disease or disorder, or any other desired alteration of a biological system. For example, an effective amount for therapeutic uses is the amount of the composition comprising a fig or a fig extract disclosed herein required to provide a clinically significant improvement in sleep adequacy or sleep quantity. An appropriate "effective" amount in any individual case may be determined by one of ordinary skill in the art using routine experimentation.

As used herein, the terms "treatment" or "treat" are interchangeable and are meant to indicate a postponement of development of restless leg syndrome and/or a reduction in the severity of such symptoms that will or are expected to develop. Also included is the treatment or prevention of sleep disorders or abnormality, and the improvement of sleep quantity or adequacy. The terms further include ameliorating existing symptoms of restless leg syndrome, preventing additional symptoms, alleviating or preventing the symptoms of sleep disorders (e.g., sleep disturbance), ameliorating or preventing the underlying metabolic or physiological causes of signs and symptoms of restless leg syndrome and sleep disorders. Also included is a method for improving sleep quantity and adequacy by administering to a subject in need of a therapeutically effective amount of a fig or fig extract. Also included is a method for improving unwanted limb movements by administering to a subject in need of a therapeutically effective amount of a fig or fig extract.

As used herein, the terms "improve", "improving" and "improvement" of a disease or disorder in a subject all refer to making subjective and/or objective measures of the disease or disorder better. For example, the terms "improve", "improving" and "improvement" of sleep in a subject all refer to making subjective and/or objective measures of sleep better. For example, increased sleep quantity is an objective measure of improved sleep in a patient suffering from restless leg syndrome. As used herein, the term "improve" with respect to sleep, is meant to reduce, reverse (e.g., alleviate), prevent (e.g., prophylaxis), ameliorate, control or manage sleep disorders or abnormalities, such as the sleeplessness and/or other signs and symptoms associated with restless leg syndrome.

As used herein, the phrases "sleep disorders," "sleep abnormality," "sleep quantity", and "sleep adequacy," have meanings normally ascribed to them in the art. "Sleep quantity" and "sleep adequacy" parameters can be measured and quantified by art-recognized tools, e.g., the Revised Medical Outcomes Study Sleep Scale (MOS Sleep-R). Examples of "sleep disorders" or "sleep abnormalities" include: primary insomnia; secondary insomnia; situational insomnia; transient insomnia; short-term insomnia; chronic insomnia; acute insomnia; prolonged latency to sleep onset; difficulty falling asleep; difficulty staying asleep; sleep maintenance abnormalities, including without limitation, frequent awakenings, increased wake time after sleep onset, sleep fragmentation, sleep disturbance, snoring, shortness of breath, transient micro-arousals, and unrefreshing sleep; increased time awake during the sleep period; waking up earlier than desired; reduced total sleep time; delayed sleep phase disorder; advanced sleep phase disorder; non-24-hour sleep-wake disorder; irregular sleep wake rhythm, disturbed paradoxical sleep, hypopnea syndrome; idiopathic hypersomnia; persistent episodic hypersomnia, alcoholic insomnia; excessive daytime sleepiness; rapid eye movement sleep behavior disorder; shift work sleep disorder; desynchronosis (jet lag); circadian rhythm sleep disorders; delayed sleep phase disorder; advanced sleep phase disorder; sleep apnea; Kleine-Levin syndrome; DiGeorge syndrome; narcolepsy; cataplexy; somnambulism; somniphobia; upper airway resistance syndrome; restless leg syndrome; periodic limb movement disorder; parasomnias including without limitation, bruxism, catathrenia, night terrors (Pavor nocturnus), nocturia, sleep enuresis, exploding head syndrome, bedtime eating disorder (BED), rapid eye movement (REM) behavior disorder, nocturnal sleep-related eating disorder (NSRED), somniloquy, and sexsomnia.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which the material is contained.

As used herein, the terms "subject," "individual," and "patient" may be used interchangeably and refer to a mammal, preferably a human; yet also domesticated mammals (e.g., canine or feline), farm mammals (e.g., equine, bovine, porcine, ovine), and laboratory/experimental mammals (e.g., mouse, rat, rabbit, hamster, guinea pig, monkey). The terms "subject," "individual," and "patient" do not denote a particular gender or age. When the compositions or methods of the invention are used to treat or prevent restless leg syndrome or sleep disorders, or to improve sleep adequacy or quantity, exemplary subjects are not otherwise in need of treatment with a fig or a fig extract. An exemplary subject treated with the compositions or methods of the invention is one who is not otherwise in need of treatment with an extract of *Ficus Carica* fruit (i.e., fig extract). A further exemplary subject treated with the compositions/methods of the invention is one who experiences personal difficulty falling asleep at night. A yet further exemplary subject treated with the compositions/methods is one who experiences personal difficulty falling asleep at night and also suffers from restless leg syndrome.

As used herein, the term "fig" means the fruit of the plant *Ficus carica*. A fig comprises the whole or partial fig fruit, and/or the fig fruit skin, and/or the fig fruit pulp, and/or the fig fruit juice. The fig may be juiced to separate juice from the fruit by squeezing or other means. The fig comprises the residues of fruit left over from juicing, also called pomace.

As used herein, the term "fig extract" means an extract comprising fig. A fig extract may be in the form of a crude extract or a solvent-soluble extract or fraction of the fig. An extract may be in the form of a solution, a concentrate, a powder, and the like. A fig tincture is an alcoholic extract of a fig. The tincture is typically comprised of various ethanol concentrations, 25% being preferred. Alternative solvents may include vinegar, glycerol, diethyl ether and propylene glycol. Ethanol has advantages of being an excellent solvent for both acidic and basic (alkaline) constituents.

As used herein, "nutraceutical" refers to a natural substance that provides health benefits or possesses medicinal value. Nutraceuticals comprise vitamins, minerals, herbs, herbal extracts, fruit, fruit extracts, vegetables, vegetable extracts, animal products, and functional foods (i.e., foods that tout a health benefit or medicinal value).

As used herein, the terms "optional" or "optionally" mean that the subsequently described event or circumstance may or may not occur, and that the description includes instances where the circumstance or event occurs and instances where the circumstance or event does not. For example, the phrase "optionally an additional pharmacologically active compound" means that the subject may or may not be given a drug other than the fig or the fig extract.

As used herein, "additional pharmacologically active compound" means any chemical material or compound suitable for administration to a mammal, preferably human, which induces a desired local or systemic effect, such as, for example: narcotics, dopamine agonists, benzodiazepines, clonidine, gabapentin, melatonin, magnesium, iron, potassium, and vitamins. General examples of pharmacologically active compounds include: anorexics; anti-infectives and antiviral agents (e.g., antibiotics); analgesics; anti-arrhythmics; anti-arthritics; anti-asthma agents; anti-cholinergics; anti-convulsants; anti-diabetic agents; anti-diarrheals; anti-depressants, anti-helminthics; anti-histaminics; anti-inflammatories; anti-migraine agents; anti-nauseants; anti-neoplastics; anti-oxidants; anti-Parkinsonism agents; anti-pruritics; anti-psychotics; anti-pyretics; anti-spasmodics; cardiovascular preparations (e.g., beta-blockers); anti-hypertensives; anxiolytics, central nervous system (CNS) stimulants; cold/cough preparations (e.g., dextromethorphan, doxylamine succinate); diuretics; eugeroics; gastrointestinal drugs (e.g., ranitidine); sympathomimetics; hormones (e.g., corticosteroids), hypnotics; immune-suppressive agents; muscle relaxants; neuroprotectants; parasympatholytics; psychostimulants; sedatives; tranquilizers; thrombolytics; vasoconstrictors and vasodilators.

As used herein, the term "restless leg syndrome" encompasses a disorder that typically occurs during sleep or rest, or just before sleep or rest, or periods of inactivity, and which is characterized by uncomfortable sensations in the legs. Examples of uncomfortable sensations in the legs include, but are not limited to, pulling, drawing, crawling, wormy, boring, tingling, pins and needles, prickly and sometimes painful sensations that are usually accompanied by an overwhelming urge to move the legs. Sleep patterns may be disturbed as individuals suffering from restless leg syndrome typically have trouble falling and maintaining sleep. Patients with restless leg syndrome are also more likely to suffer from depression and anxiety. As used herein, the term "restless leg syndrome" also encompasses acromelalgia, Ekbom Syndrome, Wittmaack-Ekbom Syndrome, nocturnal myoclonus, periodic limb movements in sleep, and periodic limb movement disorder.

As used herein, "kit" means a collection of at least two components constituting the kit. The components identified together constitute a functional unit for a given purpose. Individual member components may be physically packaged together or physically packaged separately. For example, a kit comprising an instruction for using the kit may or may not physically include the instruction with other individual member components. Instead, the instruction can be supplied as a separate member component, either in a electronic format or paper format which may be supplied on a computer readable memory device or downloaded from another source (e.g., an internet website), or as a recorded presentation.

As used herein, an "instruction" or "instructions" mean a document or documents describing relevant materials or methodologies pertaining to a kit. The materials or methodologies may include any combination of the following: background information, list of components and component availability information, such as purchase information and the like, brief or detailed protocols for usage of the kit, trouble-shooting information, reference information, safety and sterility information, technical support information, and any other related documentation. An instruction can be supplied with the kit or as a separate member component, either as a paper form or an electronic form which may be supplied on computer readable memory device or downloaded from an internet website, or as recorded presentation. An instruction can comprise one or more documents, and an instruction is meant to optionally include one or more future updates.

The present invention discloses compositions and methods for the treatment or prevention of restless leg syndrome. The compositions of the invention comprise the fig or the fig extract. The methods of the invention comprise administering to a patient in need of such treatment or prevention a therapeutically effective amount of fig or fig extract in order to treat or prevent restless leg syndrome, or a symptom or cause thereof.

In one aspect of the invention, methods of treating or preventing restless leg syndrome are provided, which comprise administering to a subject in need of such treatment or prevention a therapeutically or prophylactically effective amount of a fig or fig extract. In another aspect of the invention, the methods comprise administering to a subject in need of such treatment or prevention a therapeutically or prophylactically effective amount of a fig or fig extract in combination with at least one compound falling within the classification(s) of anxiolytics, hypnotics or sedatives.

In various embodiments, the invention methods include administering a composition including a fig or fig extract in combination with benzodiazepines (e.g., clonazepam), pergolide, carbidopa, levodopa, oxycodone, carbamazepine, gabapentin, magnesium, iron, tryptophan, theanine, melatonin, valerian root (*Valeriana officinalis*), skullcap (*Scutellaria baicalensis*), glycine, GABA (gamma-amino butyric acid), green tea (*Camellia sinensis*), chamomile (*Matricaria chamomilla*), hops (*Humulus lupulus*), passionflower, lemon balm, or vitamins (e.g. vitamin B12). The present invention also provides such compositions.

In various embodiments, the invention methods include administering a composition including a fig or fig extract in combination with one or more of the following herbs (or herbal extracts thereof): achyranthes (*Achyranthes aspera*), aloe (*Aloe barbadensis, Aloe ferox, Aloe vera*), anise (*Pimpinella anisum*), aristolochia (*Aristolochia bracteolata*), arnica (*Arnica fulgens*), banyan, *Ficus bengalensis*, bakula (*Mimusops elengi*), basil (*Ocimum basilicum, Ocimum minimum*), betel, (*Piper betle*), black pepper, (*Piper nigrum*), camphor (*Cinnamomum camphora*), catechu (*Acacia catechu*), celandine, chebula (*Terminalis chebula*), cinnamon (*Cinnamomum lourerii* and *Cinnamomum zeylandicum*), citrus, clove (*Syzygium aromaticum*), dill, echinacea (*Echinacea pallida*), eucalyptus, (*Eucalyptus globulus*), fennel (*Foeniculum vulgare*), gardenia (*Gardenia jasminoides*), ginger (*Zingiber officinale*), grape (*Vitis vinifera*), houttuynia (*Houttuynia cordata*), Indian mulberry (*Morinda citrifolia*), juniper (*Juniperus communis*), lemongrass, licorice, long pepper (*Piper longum*), madhuca (*Madhuca longifolia*), magnolia (*Magnolia officinalis*), marigold (*Calendula officinalis*), mastic (*Pistacia lentiscus*), melilot (*Melilotus officinalis*), milfoil (*Achillea millefolium*), myrrh, neem (*Azadirachta indica*) neroli, nutmeg (*Myristica fragrans*), oak gall (*Quercus infectoria*), oolong tea, parsley (*Petroselinum sativum*), peelu (*Salvadora persica*), peppermint (*Mentha piperita*), pine, pomegranate (*Punica granatum*), prickly acacia (*Acacia nilotica*), rhatany, rosemary (*Rosmarinus officinalis*), saffron (*Crocus sativus*), sage, sandalwood, spearmint (*Mentha spicata*), spilanthes (*Spilanthes calvi*), star anise (*Illicium verum*), thyme, tomar (*Zanthoxylum armatum*), tulsi (*Ocimum sanctum*), turmeric (*Curcuma longa*), usnea (*Usnea barbata*), vajradanti (*Potentilla fulgens*), walnut (*Juglens regia*), or wintergreen (*Gaultheria procumbens*). The present invention also provides such compositions.

The invention provides a method of treating or preventing restless leg syndrome at night—during or prior to sleep—and during the day, e.g., at rest during the day or during periods of inactivity. The method includes administering to a subject with restless leg syndrome a therapeutically effective amount of a fig or a fig extract.

The present invention also provides compositions and methods for ameliorating, treating or preventing sleep disorders and abnormalities and/or improving sleep quantity or adequacy. The methods of the present invention include administering to a subject in need to such treatment, prevention or improvement a fig or a fig extract in a therapeutically effective amount. In various embodiments, the methods do not induce or require sedation. In an exemplary embodiment, the present invention provides a method producing improved onset and duration of sleep. In a further embodiment, the present invention provides a method of producing increased duration of sleep.

Exemplary methods of the invention comprise administering to a subject in need of such treatment or prevention of sleep disorder or abnormality or improvement in sleep quantity or adequacy a therapeutically or prophylactically effective amount of a fig or fig extract in combination with at least one compound falling within the classification(s) of anxiolytics, hypnotics or sedatives.

According to the present invention there is provided the use of fig or fig extract in the manufacture of a medicament for use in the treatment or prevention of restless leg syndrome, sleep disorder or abnormality, or in the improvement of sleep quantity or adequacy.

Fig can be prepared by any one of the general methods well known to the skilled person. Fig extract can be prepared by any one of the general methods well known to the skilled person. In various embodiments, the fig or the fig extract may be prepared in a variety of forms, such as, for example, fresh, dried, heated, frozen, freeze-dried; as a powder, paste, gel, jam, jelly, gelato, lip gloss, cream, ointment, drops, tincture, pill, tablet, butter, syrup, gum, hard candy, soft candy, gummy candy, taffy, toffee, cough drop, lozenge, aerosolized spray, fruit leather, newton, melt-away, bar, cookie, and yogurt; as a beverage (e.g. an alcoholic/fermented beverage); and the like.

In one embodiment the fig extract is prepared by a process comprising step (i) defined below. In a further embodiment the fig or fig extract is prepared by a process comprising steps (i) to (ii) defined below. In a yet further embodiment the fig or fig extract is prepared by a process comprising steps (i) to (iii) defined below. In a yet further embodiment the fig or fig extract is prepared by a process comprising steps (i) to (iv) defined below. In a yet further embodiment the fig or fig extract is prepared by a process comprising steps (i) to (v) defined below. In a yet further embodiment the fig or fig extract is prepared by a process comprising steps (i) to (vi) defined below.

In another aspect, the invention provides a process for preparing fig fruit extract, comprising the following steps: (i) (i.e., the first step) contacting whole fig fruit, and/or fig fruit skin, and/or fig fruit pulp, and/or residues of fig fruit (retained from fig fruit juicing), with an organic solvent, water or an aqueous/organic solvent to provide an aqueous, organic or aqueous/organic extract and a solid residue; and optionally, (ii) (i.e., the second step) separating the aqueous, organic or aqueous/organic extract from the solid residue to give a crude aqueous, organic or aqueous/organic fig extract; and optionally, (iii) (i.e., the third step) evaporating the crude aqueous, organic or aqueous/organic fig fruit extract from the second step to give a substantially aqueous fig extract concentrate and a precipitate; and optionally, (iv) (i.e., the fourth step) separating the substantially aqueous fig extract concentrate from the precipitate; and optionally, (v) (i.e., the fifth step) contacting the substantially aqueous fig extract from the fourth step with a polymeric resin to adsorb at least one component from the substantially aqueous fig extract; and optionally, (vi) (i.e., the sixth step) eluting at least one component from the resin with an organic solvent or a mixture of organic solvents to obtain a fig extract.

In another embodiment the substantially aqueous fig extract concentrate from the fourth step may be dried and dissolved in a mixture of an organic solvent and water, for example 65:35 ethanol:water (i.e., 65% ethanol to 35% water per unit volume of fig extract). The fruit sugars and other polar material are not soluble in the organic solvent. Drying the organic solvent and water mixture will provide a fig extract that is more concentrated. The drying procedure can be repeated several times to further concentrate the fig extract.

In another embodiment the substantially aqueous fig extract concentrate from the fourth step may be dissolved in a non-water miscible solvent, such as ethyl acetate to yield a non-aqueous fig extract.

In yet another embodiment, the invention provides a process for preparing fig extract by contacting whole fig fruit, and/or fig fruit skin, and/or fig fruit pulp and/or residues of fig fruit from fig fruit juicing, with an organic solvent, water or an aqueous/organic solvent to provide an aqueous, organic or aqueous/organic extract and a solid residue; and separating the solid residue from the aqueous, organic or aqueous/organic extract to give a solid residue.

In yet another embodiment, the fig extract is a free-flowing powder. In a further embodiment, the fig extract produced by the process of the present invention can be vacuum-dried, spray-dried or freeze-dried to produce the free-flowing powder.

In yet another embodiment, the whole fig fruit, and/or fig fruit skin and/or fig fruit pulp and/or residues of fig fruit left over after juicing of the fruit may optionally be minced, mashed, crushed, pressed, blended, pureed, sliced or chopped prior to the first step. The fruit or fruit portions may be frozen and thawed prior to the first step. The fruit or fruit portions may be heated and/or cooled prior to the first step. The fruit or fruit portions may also be dried or freeze-dried prior to the first step.

In yet another embodiment, the fig may be juiced (the juice removed from the fruit by squeezing or other means) prior to the first step, thereby providing residues of fig (i.e., the remainder or remainder portion of fruit after the juice is removed from the fruit), which can be used in the first step (or added in prior to or during any of the steps). Juicing can be carried out using a centrifuge, mechanical press, or screw press, or other method known in the art. The de-juicing operation may be combined with an enzyme pre-treatment to assist in the release of juice from the fruit or parts thereof.

In yet another embodiment, the organic solvent used in the process for preparing fig fruit extract is acetone or an alcohol such as methanol, ethanol, isopropyl alcohol or 1-propanol. Where an aqueous/organic solvent is used, the organic solvent and water can be used in any suitable proportions, such as about 20-95% water.

In yet another embodiment, the substantially aqueous fig fruit extract concentrate from the fourth step is fractionated by contact with a polymeric resin. The resin absorbs at least one component from the extract concentrate. The component(s) can then be eluted from the resin with an organic solvent or mixture of organic solvents to give the fig fruit extract of the present invention. The polymeric resin may optionally be washed with distilled water prior to eluting the at least one component. In an exemplary embodiment, the polymeric resin is a non-ionic polymeric adsorbent resin.

The following embodiments provide exemplary methods of preparing fig fruit extract of the invention.

Example 1: Preparation of Fig Fruit Extract

The extract of fig was prepared and isolated from fresh fig fruit. Whole fig fruit, skin, flesh, fruit residues left from juicing operations or various mixtures of these were minced in a blender. To the resulting pulp was added approximately an equal volume of water, alcohol, a water miscible organic solvent such as acetone or an aqueous mixture of alcohol or organic solvent. In this example, food grade ethanol was used. The mixture was stirred occasionally during the first hour and left to soak overnight. The mixture was filtered and the filtrate concentrated at 39° C. under vacuum. The concentrate was filtered to remove any precipitated material and then passed through a column of polymeric resin. Distilled water was passed through the column to remove sugars and other polar materials. The absorbed compounds were eluted from the column with ethanol and concentrated under reduced pressure to give a concentrate. The concentrate was freeze-dried to give the fig fruit extract as a light gold powder. In one embodiment the powder of fig extract is provided for oral administration.

Example 1: Preparation of a Fig Extract

The extract of fig was prepared and isolated from fresh fig. Whole fruit, skin, flesh, fruit residues or various mixtures or fractions thereof left over from juicing operations were minced in a blender. Coconut oil is added to the resultant minced pulp at a 1:4 ratio (i.e., 1 unit coconut oil to 4 units minced pulp). The resultant minced pulp and coconut oil mixture is then cut into squares (e.g., one centimeter by one centimeter by one centimeter squares) to give bars. In one embodiment the bar of fig extract is provided for oral administration.

Advantageously, the fig fruit extract of the invention can be provided to a patient in a variety of forms. For example, the fig fruit extract can be provided as a nutraceutical, e.g. a dietary supplement. Alternatively, the fig fruit extract can be provided as a food product, e.g. as part of a functional food or beverage. The fig fruit extract of the invention can be provided as an adjunct to conventional treatments. As a natural food ingredient, fig or fig extract is unlikely to produce undesirable side-effects such as interfering with conventional pharmaceutical treatment efficacy. The typically pleasing aroma and taste of fig or fig extract is likely to increase subject compliance with conventional pharmaceutical treatments.

Alternatively, the fig or the fig extract can be provided as a pharmaceutical composition. The extract may be formulated into solid or liquid preparations such as tablets, capsules, suppositories, powders, solutions, suspensions and dispersions. In some embodiments the fig fruit extract is formulated for oral administration as solid or liquid preparations, for example tablets, capsules, powders, solutions, suspensions or dispersions. Such preparations are well known in the art as are other oral dosage regimes not listed herein. In the tablet form the fig fruit extract may be tableted with conventional tablet bases such as lactose, sucrose and corn starch, together with a binder, a disintegration agent and a lubricant. The binder may be, for example, corn starch or gelatin, the disintegrating agent may be, for example, potato starch or alginic acid, and the lubricant may be, for example, magnesium stearate. For oral administration in the form of capsules, diluents such as lactose and dried corn starch may be employed. Other components such as colorings, sweeteners, flavors, preservatives, may optionally be added.

When aqueous suspensions are required for oral use, the fig extract may be combined with carriers such as water and ethanol, and emulsifying agents, suspending agents and/or surfactants may be used. Colorings, sweeteners, preservatives, or flavorings may also be added.

The fig or the fig extract may further be administered by means of sustained release systems. For example, the fig or the fig extract may be incorporated into a slowly dissolving tablet or capsule. Liquid forms include carriers such as water and ethanol, with or without other agents such as pharmaceutically acceptable surfactants or suspending agents.

In one aspect the invention provides a dosage unit comprising about 350 mg fig or fruit extract. In another aspect, the invention comprises a dosage unit consisting essentially of 350 mg fig fruit extract. Preferably, the dosage unit is a tablet.

The amount of fig or fig extract that can be combined with one or more excipients to produce a single dosage form may vary depending upon the subject and the particular route of administration.

In various embodiments, a subject is dosed with the fig or fig extract at a single bolus dosage with no dosing period. In various embodiments, a subject is dosed with the fig or fig extract at a loading dosage (i.e., induction dosage) for a first dosing period. Following the first dosing period, the subject is provided a fig or fig extract dosage lower than the loading dosage for a second dosing period. In various embodiments, the fig or fig extract is administered once every fifteen minutes, once every half hour, once every hour, once ever 4 hours, once every 12 hours, once every day, once every two days, once every three days, once every four days, once every week, or even less frequently.

Generally, a formulation intended for oral administration to humans will generally contain for example from about 0.1 mg to about 1500 mg of the active agent (e.g., fig or fig extract), preferably about 1 mg to about 1000 mg per dose of the active agent combined with an appropriate amount of excipient(s). However, exemplary dosage unit forms generally contain about 5 mg to about 800 mg, from about 25 to about 600 mg, from about 50 to about 550 mg, from about 75 to about 525 mg, from about 100 to about 500 mg, from about 225 to about 450 mg and from about 300 to about 375 mg of fig or fig extract.

In various embodiments, the invention provides an oral formulation for administration to humans having from about 0.1 mg to about 1500 mg of the active agent (e.g., fig or fig extract), for example, from about 1 mg to about 1000 mg, which is optionally combined with an appropriate amount of excipient(s).

In various embodiments, the invention provides an oral unit dose formulation for administration to humans having from about 300 mg to about 400 mg of the active agent (e.g., fig). This unit dosage form can be a daily dosage form or can be administered less than daily (e.g., once every other day).

More specifically, a formulation comprising fig or fig extract, for example, intended for oral administration to humans will generally contain for example from about 0.2 mg to about 30,000 mg of active agent (i.e., fig or fig extract) combined with an appropriate amount of excipient(s), more preferably, about 0.7 mg to about 20,000 mg, from about 1.5 to about 10,000 mg, from about 2.5 to about 5,000 mg, from about 3 to about 2,500 mg, from about 4 to about 2,000 mg, from about 5 to about 1,200 mg and from about 10 to about 800 mg of fig or fig extract.

However, it will be readily understood that it may be necessary to vary the dose of the fig or fig extract administered in accordance with well known medical practice in order to take account of the nature and severity of the condition or disease under treatment, any concurrent therapy, and of the age, weight, genotype and sex of the patient receiving treatment.

Generally, in therapeutic use, it is envisaged that a composition according to the invention would be administered so that a dose of the fig or fig extract is received which is generally in the range of about 0.1 to about 1500 mg/day, about 1 to about 1000 mg/day, about 5 to about 800 mg/day and about 25 to about 600 mg/day of active agent daily given, if necessary in divided doses.

More specifically, for a composition comprising fig or fig extract, in therapeutic use, a composition according to the invention is administered so that a dose of the fig or fig extract (or of an equivalent amount of a pharmaceutically acceptable salt thereof) is received which is generally in the range 0.1 to 1500 mg/day. More specifically, from between 1 to 1000 mg/day and 5 to 800 mg/day or 25 to 600 mg of fig or fig extract daily given if necessary in divided doses.

More specifically, for a composition comprising fig or fig extract, in therapeutic use, it is envisaged that a composition according to the invention could be administered intermittently, on a regimen of hourly, daily, alternate days, twice weekly or weekly, so that a dose of the fig or fig extract is received which is generally in the range 0.1 to 1,100 mg/week. More specifically, from between 1 to 1000 mg/week and 25 to 600 mg/day of fig or fig extract. The preferred regimen would provide the lowest effective concentration of the fig or the fig extract which improves the condition of the patient. For example, the preferred regimen is a regimen that would provide the lowest effective concentration of the fig or the fig extract to treat or prevent restless leg syndrome or sleep disorders, or improve sleep quantity or adequacy, in a subject in need thereof.

In a still further aspect of the invention there is provided a method of treating and/or preventing restless leg syndrome comprising administering to the patient a pharmaceutically effective amount of a fig or a fig extract.

In a particular embodiment of the invention said disease is treated. In a still further embodiment of the invention the patient is a human being. In a still further embodiment of the invention the disease can be restless leg syndrome, Ekbom Syndrome, Wittmaack-Ekbom Syndrome, acromelalgia, nocturnal myoclonus, periodic limb movements in sleep, and periodic limb movement disorder. In a still further embodiment of the present invention said fig or fig extract is as described above.

While the compound of the present invention has a superior effect even when used solely, the effect can be further promoted by using the compound in combination with other pharmaceutical preparations and therapies. Examples of the preparation and therapy to be combined include, but not limited to benzodiazepines, pergolide, carbidopa, levodopa, oxycodone, gabapentin, melatonin, magnesium, iron, vitamins, valerian root, chamomile, hops, passionflower, mint, lemon balm, hypnotics, sedatives, narcotics, dopamine agonists, or pharmaceutically acceptable salts, solvates, prodrugs, optically and pharmacologically active stereoisomers thereof. Preferably, the combination has a synergistic effect.

As one of skill in the art will recognize, the timing of administering the dosage containing the fig or the fig extract can vary. In one aspect of the invention, the fig or the fig extract are administered after the identification of symptoms of restless leg syndrome. The administration of the fig or the fig extract can be initiated after the onset of the symptoms. In another aspect of the invention, the fig or the fig extract is administered to the patient concurrently with an additional pharmacologically active compound. Preferably, the fig or the fig extract is administered for about 1 month to about 3 months to facilitate recovery. Preferably, the compounds, and compositions comprising the compounds are administered up to about 12 months or longer, or, even more preferably, administered continuously.

In another aspect of the invention, the fig or the fig extract are administered prophylactically to patients with a predisposition towards restless leg syndrome. The administration of the fig or the fig extract can be initiated before the onset of the symptoms. In another aspect of the invention, the fig or the fig extract are administered to the patient concurrently with an additional pharmacologically active compound. Preferably, the fig or the fig extract is administered for about 1 month to about 3 months to facilitate prophylaxis. Preferably, the fig or the fig extract is administered up to about 12 months or longer, or, even more preferably, administered continuously. In one embodiment, the fig or the fig extract is administered prophylactically to a subject with a predispositive personal family history of restless leg syndrome. In another embodiment, the fig or the fig extract is administered prophylactically to a subject with a predispositive personal genetic risk factor or risk factors of restless leg syndrome. In a further embodiment, the fig or the fig extract is administered prophylactically to a subject identified as having a single nucleotide polymorphism allele linked with restless leg syndrome.

The methods described herein use pharmaceutical compositions comprising the fig or fig extracts described above, where the compositions preferably comprise fig or fig extract, optionally in combination with another compound with which it has synergistic effect, together with one or more pharmaceutically acceptable excipients or vehicles, and optionally other therapeutic and/or prophylactic ingredients. Such excipients include liquids such as water, saline, glycerol, polyethylene glycol (PEG), hyaluronic acid, ethanol, etc. Suitable excipients for non-liquid formulations are also well-known to those of skill in the art.

Additionally, auxiliary substances, such as emulsifying or wetting agents, surfactants, biological buffers, and the like, may be present in such vehicles. A biological buffer can be virtually any solution which is pharmacologically acceptable and which provides the formulation with the desired pH, e.g., an acidity and alkalinity within the physiologically acceptable range. Typical examples of buffer solutions include saline, Hanks buffered saline, phosphate buffered saline, Tris solution, and the like.

Depending on the intended mode of administration, the pharmaceutical compositions may be in the form of solid, semi-solid or liquid dosage forms, such as, for example, tablets, pills, capsules, powders, liquids, suspensions, creams, or the like, preferably in unit dosage form suitable for single administration of a precise dosage. The compositions will include an effective amount of the selected fig or the selected fig extract in combination with a pharmaceutically acceptable carrier and, in addition, may include other pharmaceutical agents, adjuvants, diluents, buffers, etc. The present invention includes a pharmaceutical composition comprising a fig or fig extract together with one or more pharmaceutically acceptable carriers, and optionally other therapeutic and/or prophylactic ingredients.

One or more other pharmaceutically acceptable carriers, excipients or stabilizers such as those described in reference work Remington's The Science and Practice of Pharmacy, 21st edition, Gerbino et al. (Philadelphia, Pa.: Lippincott Williams & Wilkins, 2005) may be included in a formulation of the present invention provided that the carriers, excipients or stabilizers do not adversely affect the desired characteristics of the formulation. Said reference work incorporated herein by reference.

In general, the compounds of this invention will be administered in a therapeutically effective amount by any of the accepted modes of administration. Suitable dosage ranges depend upon numerous factors such as, for example, the severity of the disease to be treated, the age and relative health of the subject, the potency of the compound or compounds used, the route and form of an administration, the indication towards which the administration is directed, and/or the preferences and experience of a medical or healthcare practitioner. One of ordinary skill in the art of treating such diseases will be able, without undue experimentation and in reliance upon personal knowledge and the disclosure of this application, to ascertain a therapeutically effective amount of the compounds of this invention for a given disease.

The pharmaceutical compositions and dosage forms of this invention are particularly useful in the methods herein, and may be suitable for oral or mucosal (e.g., nasal, sublingual, and buccal) administration.

Preferred pharmaceutical compositions and dosage forms comprise fig or fig extract in an amount from about 0.1 mg to about 1500 mg, preferably from about 1 mg to about 1000 mg, and more preferably from about 25 mg to about 600 mg. Pharmaceutical compositions and dosage forms of the invention typically also comprise one or more pharmaceutically acceptable excipients or diluents.

Single unit dosage forms of the invention are suitable for oral or mucosal (e.g., nasal, sublingual, or buccal) to a patient. Examples of dosage forms include, but are not limited to: tablets; caplets; capsules, such as soft elastic gelatin capsules; cachets; troches; lozenges; dispersions; pastes; powders; creams; solutions; patches; aerosols (e.g., nasal sprays or inhalers); gels; liquid dosage forms suitable for oral or mucosal administration to a patient, including suspensions (e.g. aqueous or non-aqueous liquid suspensions, oil-in-water emulsions, or a water-in-oil liquid emulsions), solutions, and elixirs; and solids (e.g., crystalline or amorphous solids) that can be reconstituted to provide liquid dosage forms suitable for oral or mucosal administration to a patient.

Pharmaceutical compositions of the present invention that are suitable for oral administration can be presented as discrete dosage forms, such as, but are not limited to, tablets (e.g., chewable tablets), caplets, capsules, and liquids (e.g., flavored syrups). In one embodiment, fig or fig extract may be administered via microspheres for oral administration. Such dosage forms contain predetermined amounts of fig or fig extract, and may be prepared by methods of pharmacy well known to those skilled in the art.

Typical oral dosage forms of the invention are prepared by combining fig or fig extract in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, fillers, and disintegrating agents.

A tablet can be prepared by compression or molding. Compressed tablets can be prepared by compressing in a suitable machine a fig or fig extract in a free-flowing form such as powder or granules, optionally mixed with an excipient. Molded tablets can be made by molding in a suitable machine a mixture of the powdered fig or fig extract, optionally mixed with an excipient, moistened with an inert liquid diluent.

Binders suitable for use in pharmaceutical compositions and dosage forms include, but are not limited to, corn starch, potato starch, or other starches, gelatin, natural and synthetic gums such as sodium alginate, alginic acid, shiraz gum, guar gum (guaran), gum arabic (acacia), cellulose and its derivatives (e.g., ethyl cellulose, cellulose acetate, carboxymethyl cellulose calcium, sodium carboxymethyl cellulose), methyl cellulose, pre-gelatinized starch, hydroxypropyl methyl cellulose, microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates/dextrans, kaolin, mannitol, silicic acid, sorbitol, starch, pre-gelatinized starch, and mixtures thereof. The binder or filler in pharmaceutical compositions of the invention is typically present in from about 45 to about 95 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the fig or the fig extract should be used to form solid oral dosage forms of the invention. The amount of disintegrant used varies based upon the type of formulation, and is readily discernible to those of ordinary skill in the art. Typical pharmaceutical compositions comprise from about 0.1 to about 10 weight percent of disintegrant, preferably from about 1 to about 5 weight percent of disintegrant.

Disintegrants that can be used in pharmaceutical compositions and dosage forms of the invention include, but are not limited to, agar, alginic acid, calcium carbonate, microcrystalline cellulose, tapioca starch, pre-gelatinized starch, other starches, other algins, other celluloses, other gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, syloid silica gel, ethyl oleate, ethyl laureate, and mixtures thereof. Lubricants are typically used in an amount of less than about 1 weight percent of the pharmaceutical compositions or dosage forms into which they are incorporated.

The magnitude of a prophylactic or therapeutic dose of fig or fig extract in the acute or chronic management of a restless leg syndrome disorder or condition will vary with the severity of the disorder or condition to be treated and the route of administration.

In an exemplary embodiment, the present invention provides a unit dosage formulation having an amount of a composition comprising fig or fig extract which is therapeutically effective to treat or prevent restless leg syndrome and/or its symptoms; or treat or prevent sleep disorders and/or improve sleep quantity and/or adequacy according an art-recognized measure, e.g., the Medical Outcomes Study Sleep Scale Revised (MOS Sleep-R). The unit dosage formulation optionally includes an additional pharmacologically active compound, which is efficacious in treating or preventing the disease or condition the composition comprising fig or fig extract is intended to treat or, optionally, is of use to treat a disease or condition which is co-morbid with the disease or condition the composition comprising fig or fig extract is intended to treat.

This invention further comprises kits which, when used by a patient, a medical or healthcare practitioner, or other agency of the patient, can simplify the administration of appropriate amounts of compositions comprising fig or fig extract to a patient.

A typical kit of the invention comprises a unit dosage form of a composition comprising the fig or fig extract of the invention, such as a fig or fig extract, and a unit dosage form of an additional pharmacologically active compound. Examples of additional pharmacologically active compounds are disclosed herein, for example, melatonin.

Kits of the invention can further comprise devices that are used to administer the fig or fig extract. Examples of such devices include, but are not limited to, an aerosolizer.

Kits of the invention can further comprise pharmaceutically acceptable vehicles that can be used to administer one or more fig or fig extracts. For example, if a fig or fig extract is provided in a solid form that must be reconstituted for oral administration, the kit can comprise a sealed or unsealed container of a suitable vehicle in which the fig or fig extract can be dissolved to form a solution that is suitable for oral administration. Examples of pharmaceutically acceptable vehicles include, but are not limited to: water, sodium chloride solution, dextrose solution, dextrose and sodium chloride solution; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, and benzyl benzoate.

In summary, the present invention provides:

A method of treating or preventing restless leg syndrome which comprises administering to a patient in need of such treatment or prevention a therapeutically or prophylactically effective amount of a fig or a fig extract. The invention includes, for example, treatment of restless leg syndrome during the daytime (e.g., at rest or during inactivity) or nighttime (e.g., during or prior to sleep).

A method of treating or preventing sleep disorders which comprises administering to a patient in need of such treatment or prevention a therapeutically or prophylactically effective amount of a fig or a fig extract.

A method of improving sleep quantity or sleep adequacy which comprises administering to a patient in need of such treatment or prevention a therapeutically or prophylactically effective amount of a fig or a fig extract.

A method according to any preceding paragraph which further comprises the administration of an additional pharmaceutically active compound, e.g., pergolide, carbidopa, levodopa, oxycodone, melatonin, carbamazepine, or gabapentin, or a pharmaceutically acceptable salt, solvate, hydrate, prodrug, optically and pharmacologically active stereoisomer, or pharmacologically active metabolite thereof.

A pharmaceutical composition comprising fig or fig extract.

The pharmaceutical composition according to any preceding paragraph wherein the fig or the fig extract is in an amount of from about 0.1 mg to about 1500 mg.

A pharmaceutical composition of any preceding paragraph, wherein the fig or the fig extract is in an amount of from about 1 mg to about 1000 mg.

A pharmaceutical composition of any preceding paragraph, wherein the fig or the fig extract is in an amount of from about 5 mg to about 800 mg.

A pharmaceutical composition of any preceding paragraph, wherein the fig or the fig extract is in an amount of from about 25 mg to about 600 mg.

A pharmaceutical composition according to any preceding paragraph, wherein the pharmaceutical composition is adapted for oral or mucosal administration.

A pharmaceutical composition according to any preceding paragraph for treating or preventing restless leg syndrome, the composition comprising fig or fig extract.

A pharmaceutical composition according to any preceding paragraph for treating or preventing restless leg syndrome, wherein the fig or the fig extract is present at a concentration of about 0.1 mg to about 1500.0 mg.

A pharmaceutical composition according to any preceding paragraph for treating or preventing restless leg syndrome, wherein the fig or the fig extract is present at a concentration of about 1 mg to about 1000 mg.

A pharmaceutical composition according to any preceding paragraph for treating or preventing restless leg syndrome, wherein the fig or the fig extract is present at a concentration of about 5 mg to about 800 mg.

A pharmaceutical composition according to any preceding paragraph for treating or preventing restless leg syndrome, wherein the fig or the fig extract is present at a concentration of about 25 mg to about 600 mg.

A pharmaceutical composition according to any preceding paragraph for improving sleep quantity or sleep adequacy, the composition comprising fig or fig extract.

A pharmaceutical composition according to any preceding paragraph for improving sleep quantity or sleep adequacy, wherein the fig or the fig extract is present at a concentration of about 0.1 mg to about 1500.0 mg.

A pharmaceutical composition according to any preceding paragraph for improving sleep quantity or sleep adequacy, wherein the fig or the fig extract is present at a concentration of about 1 mg to about 1000 mg.

A pharmaceutical composition according to any preceding paragraph for improving sleep quantity or sleep adequacy, wherein the fig or the fig extract is present at a concentration of about 5 mg to about 800 mg.

A pharmaceutical composition according to any preceding paragraph for improving sleep quantity or sleep adequacy, wherein the fig or the fig extract is present at a concentration of about 25 mg to about 600 mg.

A method according to any preceding paragraph wherein a daily dose of fig or fig extract is divided into two individual doses, A method according to any preceding paragraph wherein a dose of fig or fig extract is an immediate release dosage form, A method according to any preceding paragraph wherein a dose of fig or fig extract is a slow release dosage form.

A method according to any preceding paragraph wherein a dose of fig or fig extract is administered once-a-week.

A method according to any preceding paragraph wherein a dose of fig or fig extract is administered on demand.

The pharmaceutical composition or compositions of any preceding paragraph is of use in any method according to any preceding paragraph.

The applicants have surprisingly shown that administration of fig improves sleep and restless leg syndrome and reaches statistical significance when compared to placebo.

The invention is further illustrated by, though in no way limited to, the following example.

Example: measures of restless leg syndrome and sleep were assessed for fig compared to placebo in a randomized, double-blind, placebo-controlled study using conventional parameters which measure restless leg syndrome and sleep well known in the art, such as: International Restless Leg Study Group Rating Scale (IRLS), Insomnia Severity Index (ISI), Medical Outcomes Study (MOS) Sleep Scale-Revised, and Pittsburgh Sleep Diary (PSD). General descriptions of said conventional parameters are found in the following two reference works: Walters AS et al. "Validation of the International Restless Leg Syndrome Study Group rating scale for restless leg syndrome." (Sleep Medicine 2003 March; 4(2):121-32) and Smith M T and Wegener S T, "Measures of Sleep—The Insomnia Severity Index, Medical Outcomes Study (MOS) Sleep Scale, Pittsburgh Sleep Diary (PSD), and Pittsburgh Sleep Quality Index (PSQI)" (Arthritis & Rheumatism, American College of Rheumatology, Vol. 49, No. 5S, October 15, 2003,184-96); said reference works herein incorporated by reference. Fourteen subjects suffering from moderate to severe idiopathic restless leg syndrome were randomized to two groups; each group consisted of seven subjects. Two treatment arms were provided; an arm consisting of fig and another arm consisting of placebo. The first group (n=7) was orally dosed with 700 mg of fig on the first day of treatment and 350 mg of fig per day on the second through fourteenth day. The second group (n=7) was orally dosed with 700 mg of placebo on the first day of treatment and 350 mg of placebo per day on the second through fourteenth day. The total duration of treatment for each subject was fourteen consecutive days. The subjects self-assessed restless leg syndrome and sleep using IRLS, ISI, MOS Sleep-R, and PSD as tools of self-assessment. The self-assessment occurred prior to the start of treatment and again at the end of treatment. Measured daily ratings of self-assessment parameters comparing parameters measured daily from baseline (i.e., pre-treatment) to end of treatment showed decreased restless leg syndrome symptom severity and improved sleep in subjects receiving fig treatment compared to subjects receiving placebo treatment.

While not wishing to be bound by theory, the applicants posit herein: the single nucleotide polymorphism, rs9296249, located in the BTBD9 gene region (a locus encoding a BTB/POZ domain-containing protein) has previously been linked to restless leg syndrome and the higher disease frequency associated allele (T) is surprisingly discovered to be located in douroucouli (a member of the genus *Aotus* whose nocturnal diet comprises fruit of the *Ficus carica* plant) as determined through comparative mammalian genomic analyses.

Although the invention has been described by way of example, it should be appreciated that variations and modifications may be made without departing from the scope of the invention. Furthermore, where known equivalents exist to specific features, such equivalents are incorporated as if specifically referred to in the specification.

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference.

What is claimed is:

1. A method for treating restless leg syndrome, comprising;
    identifying an individual in need of treatment for restless leg syndrome;
    providing an amount of a composition comprising fig or a fig extract divided into two individual doses; and
    administering the composition to the individual in need of treatment for restless leg syndrome.

2. The method of claim 1, wherein the composition is an immediate release dosage form.

3. The method of claim 1, wherein composition is a slow release dosage form.

4. The method of claim 1, wherein the composition is administered once-a-week.

5. The method of claim 1, wherein the composition is administered daily.

6. The method of claim 1, wherein the composition is administered on demand.

7. The method of claim 1, wherein fig or fig extract is derived from *Ficus carica*.

* * * * *